(12) United States Patent
Brown et al.

(10) Patent No.: US 7,694,811 B2
(45) Date of Patent: Apr. 13, 2010

(54) MEDICAL IMPLEMENT DISTRIBUTION AND COLLECTION SYSTEM

(75) Inventors: Robert A. Brown, Algonquin, IL (US); Anton M. Smudde, Elk Grove Village, IL (US)

(73) Assignee: Covidien AG (CH)

( * ) Notice: Subject to any disclaimer, the term of this patent is extended or adjusted under 35 U.S.C. 154(b) by 541 days.

(21) Appl. No.: 11/119,967

(22) Filed: May 2, 2005

(65) Prior Publication Data

US 2006/0243618 A1 Nov. 2, 2006

(51) Int. Cl.
*B65D 83/10* (2006.01)
*A47B 81/00* (2006.01)

(52) U.S. Cl. .................. 206/366; 312/211; 232/43.2

(58) Field of Classification Search .......... 206/571, 206/229, 363–366, 359; 220/560.01, 23.2, 220/23.4, 23.83, 23.86, 23.87, 23.88, 908, 220/908.1, 909; 312/211; 232/1 E, 43.1–43.5
See application file for complete search history.

(56) References Cited

U.S. PATENT DOCUMENTS

| | | | | |
|---|---|---|---|---|
| 1,013,775 | A | * | 1/1912 | Hoffman ............ 232/1 R |
| 2,531,444 | A | * | 11/1950 | Lane ................. 312/211 |
| 3,161,341 | A | | 12/1964 | Farquhar |
| 3,889,804 | A | | 6/1975 | Ravich |
| 4,809,850 | A | | 3/1989 | Laible et al. |
| 4,863,052 | A | | 9/1989 | Lambert |
| 5,084,028 | A | | 1/1992 | Kennedy et al. |
| 5,097,950 | A | | 3/1992 | Weiss et al. |
| 5,143,210 | A | | 9/1992 | Warwick et al. |
| 5,152,394 | A | | 10/1992 | Hughes |
| 5,245,117 | A | * | 9/1993 | Withers et al. ........ 588/249 |
| 5,251,783 | A | | 10/1993 | Gringer |

(Continued)

FOREIGN PATENT DOCUMENTS

DE 538682 C 11/1931

(Continued)

OTHER PUBLICATIONS

International Search Report dated Sep. 1, 2006, application No. PCT/US2006/016736.

*Primary Examiner*—J. Gregory Pickett
(74) *Attorney, Agent, or Firm*—Lisa E. Winsor, Esq.

(57) ABSTRACT

A medical implement dispensing and disposal system is configured for mounting within an interior of an enclosure having a first opening for receiving soiled medical implements and a second opening for dispensing medical implements. The system comprises a dispensing chamber configured to be substantially enclosed within the interior of the enclosure and removed from the interior of the enclosure. The dispensing chamber is configured to contain medical implements and has an access opening for passage of medical implements from the dispensing chamber. The access opening is positioned for alignment with the second opening of the enclosure to facilitate passage of medical implements from the enclosure. The system further comprises a disposal chamber configured to be substantially enclosed within the interior of the enclosure adjacent the dispensing chamber and removed from the interior of the enclosure. The disposal chamber is further configured to collect soiled medical implements and has an inlet opening for passage of soiled medical implements into the disposal chamber. The inlet opening is positioned for alignment with the first opening of the enclosure to facilitate passage of soiled medical implements into the enclosure.

18 Claims, 10 Drawing Sheets

U.S. PATENT DOCUMENTS

| | | | |
|---|---|---|---|
| 5,405,043 A | 4/1995 | Meloney | |
| 5,494,158 A | 2/1996 | Erickson | |
| 5,662,235 A * | 9/1997 | Nieto | 220/23.86 |
| 5,706,942 A | 1/1998 | Vila et al. | |
| 5,740,909 A | 4/1998 | Nazare et al. | |
| 5,878,899 A | 3/1999 | Manganiello et al. | |
| 6,685,017 B2 | 2/2004 | Erickson | |
| 6,702,147 B2 * | 3/2004 | Ashford | 221/34 |
| 2002/0190073 A1 | 12/2002 | Hewett | |
| 2003/0132129 A1 | 7/2003 | Erickson | |
| 2003/0226851 A1 | 12/2003 | Antebi | |
| 2003/0226879 A1 | 12/2003 | Auclair et al. | |
| 2004/0099719 A1 | 5/2004 | Shadrach, III | |

FOREIGN PATENT DOCUMENTS

| | | |
|---|---|---|
| DE | 9214287 U1 | 1/1993 |
| EP | 1449491 A | 8/2004 |
| GB | 2275673 A | 9/1994 |
| WO | WO 91/01920 | 2/1991 |
| WO | WO 2005/120610 A | 12/2005 |

* cited by examiner

MEDICAL IMPLEMENT DISTRIBUTION AND COLLECTION SYSTEM

FIELD OF THE INVENTION

The present invention relates to a distribution and collection system for medical implements.

BACKGROUND OF THE INVENTION

In a hospital, doctor's office or home environment setting, soiled syringes or other medical implements are commonly deposited in a disposal container following their use. Unused, sterile syringes or other medical implements are commonly obtained from a source separate from the disposal container. It is somewhat inconvenient at times, however, to provide a source of unused, sterile medical implements and a separate container for collecting the soiled medical implements following their use. In other words, it is sometimes disadvantageous from a convenience standpoint for medical practitioners to have one location from which implements are obtained and a separate location in which implements are disposed of.

Attempts have been made to overcome this inconvenience. For example, improved syringe dispensing and collecting systems for personal use are disclosed in U.S. Pat. No. 5,152,394, which illustrates a syringe dispensing and collecting system comprising a cylindrical container having a sterile hypodermic needle storage chamber and a separate soiled hypodermic needle collection chamber. The storage chamber is maintained in an outer peripheral region of the cylindrical container and the collection chamber is maintained in a central region of the cylindrical container. The storage chamber and the collection chamber are separated by an inner cylindrical wall. A telescoping cover mounted to the top of the container defines an opening configured to accept a soiled hypodermic needle. An outer wall of the container provides an outlet opening for the passage of sterile hypodermic needles from the storage chamber.

Nevertheless, there continues to be a need to further develop and improve disposal and collection devices for medical implements.

SUMMARY OF THE INVENTION

According to an aspect of the invention a medical implement dispensing and disposal system is configured for mounting within an interior of an enclosure having a first opening for receiving soiled medical implements and a second opening for dispensing medical implements. The medical implement dispensing and disposal system comprises a dispensing chamber configured to be substantially enclosed within the interior of the enclosure and removed from the interior of the enclosure. The dispensing chamber is configured to contain medical implements and has an access opening for passage of medical implements from the dispensing chamber. The access opening is positioned for alignment with the second opening of the enclosure to facilitate passage of medical implements from the enclosure. The medical implement dispensing and disposal system further comprises a disposal chamber configured to be substantially enclosed within the interior of the enclosure adjacent the dispensing chamber and removed from the interior of the enclosure. The disposal chamber is further configured to collect soiled medical implements and has an inlet opening for passage of soiled medical implements into the disposal chamber. The inlet opening is positioned for alignment with the first opening of the enclosure to facilitate passage of soiled medical implements into the enclosure.

According to another aspect of the invention, an enclosure configured to accommodate a medical implement dispensing and disposal system having a dispensing chamber for dispensing medical implements and a disposal chamber for receiving soiled medical implements is provided. The enclosure comprises an enclosure body defining an interior configured to receive the medical implement dispensing and disposal system. An inlet opening is defined by the enclosure body, wherein the inlet opening is positioned for passage of soiled medical implements from outside the enclosure body into the disposal chamber within the interior of the enclosure body. An access opening is defined by the enclosure body, wherein the access opening is positioned for passage of medical implements from within the dispensing chamber within the interior of the enclosure body.

According to still another aspect of the invention, a medical implement dispensing and disposal system comprises an enclosure having an interior. A disposal chamber is positioned within the interior of the enclosure and defines an inlet opening for passage of soiled medical implements into the disposal chamber. A dispensing chamber is positioned within the interior of the enclosure and defines an access opening for passage of medical implements from the dispensing chamber.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
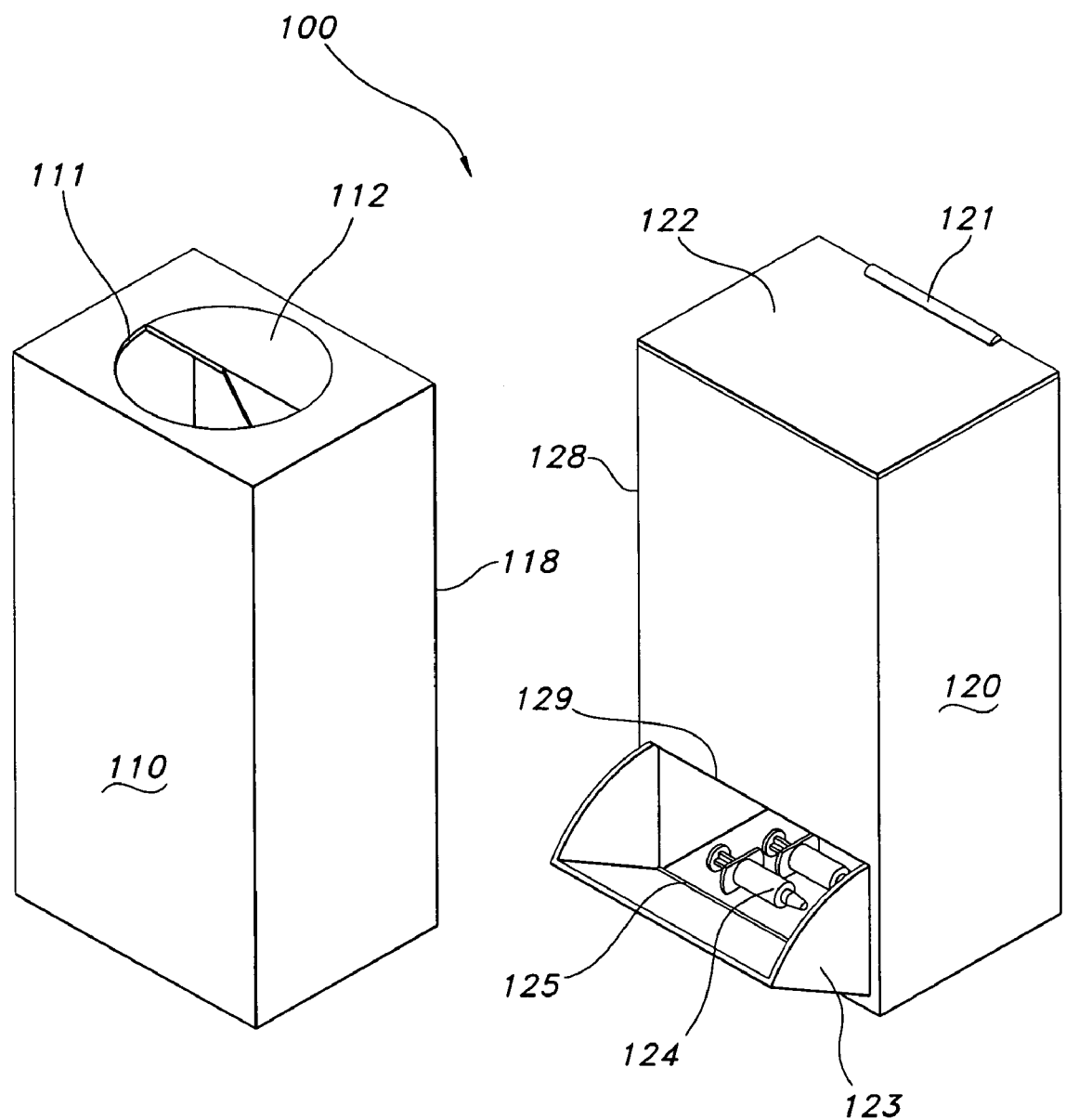
FIG. 1 is a perspective view of an embodiment of a medical implement dispensing and disposal system according to an aspect of this invention.

Although the invention is illustrated and described herein with reference to specific embodiments, the invention is not intended to be limited to the details shown. Rather, various modifications may be made in the details within the scope and range of equivalents of the claims and without departing from the invention.

The invention is best understood from the following detailed description when read in connection with the accompanying drawing figures, which shows exemplary embodiments of the invention selected for illustrative purposes. The invention will be illustrated with reference to the figures. Such figures are intended to be illustrative rather than limiting and are included herewith to facilitate the explanation of the present invention.

As used herein, the term medical implement refers to any commonly consumed device used for medical purposes, such as but not limited to a sharp, syringe, tongue depressor, lancet, scalpel, slide, pipette and the like.

Referring generally to the figures, a medical implement dispensing and disposal system 100, 200, 300 according to exemplary aspects of this invention is comprised of a medical implement dispensing container or container portion 120, 220, 310' defining a dispensing chamber; a soiled medical implement collection container or container portion 110, 210, 310 defining a collection chamber; and an optional enclosure 130, 230, 330 to house both chambers. The collection chamber defined by container 110, 210, 310 is configured to collect soiled medical implements and includes an inlet 111, 211, 317 positioned for the passage of the soiled medical implements into the collection container 110, 210, 310. The dispensing chamber defined by container 120, 220, 310' is configured to contain unused medical implements and includes an access opening 129, 223, 317 positioned for the passage of unused medical implements into the container 120, 220, 310'. The collection chamber defined by the container 110, 210, 310 and the dispensing chamber defined by the container 120, 220, 310' are separate from one another to substantially prevent the integration of soiled and unused medical implements.

The dispensing and collection chambers are housed within the enclosure 130, 230, 330 and positioned adjacent to one another. The enclosure 130, 230, 330 provides an opening 131, 231, 331 to access the inlet 111, 211, 317 of the collection chamber defined by container 110, 210, 310. The enclosure 130, 230, 330 also provides an opening 132, 232, 332 to access the access opening 129, 223, 317 of the dispensing chamber defined by container 120, 220, 310'. The enclosure 130, 230, 330 includes a locking door 135, 235, 335 to inhibit unauthorized access to the dispensing container 120, 220, 310' and the collection container 110, 210, 310.

Figure 4:
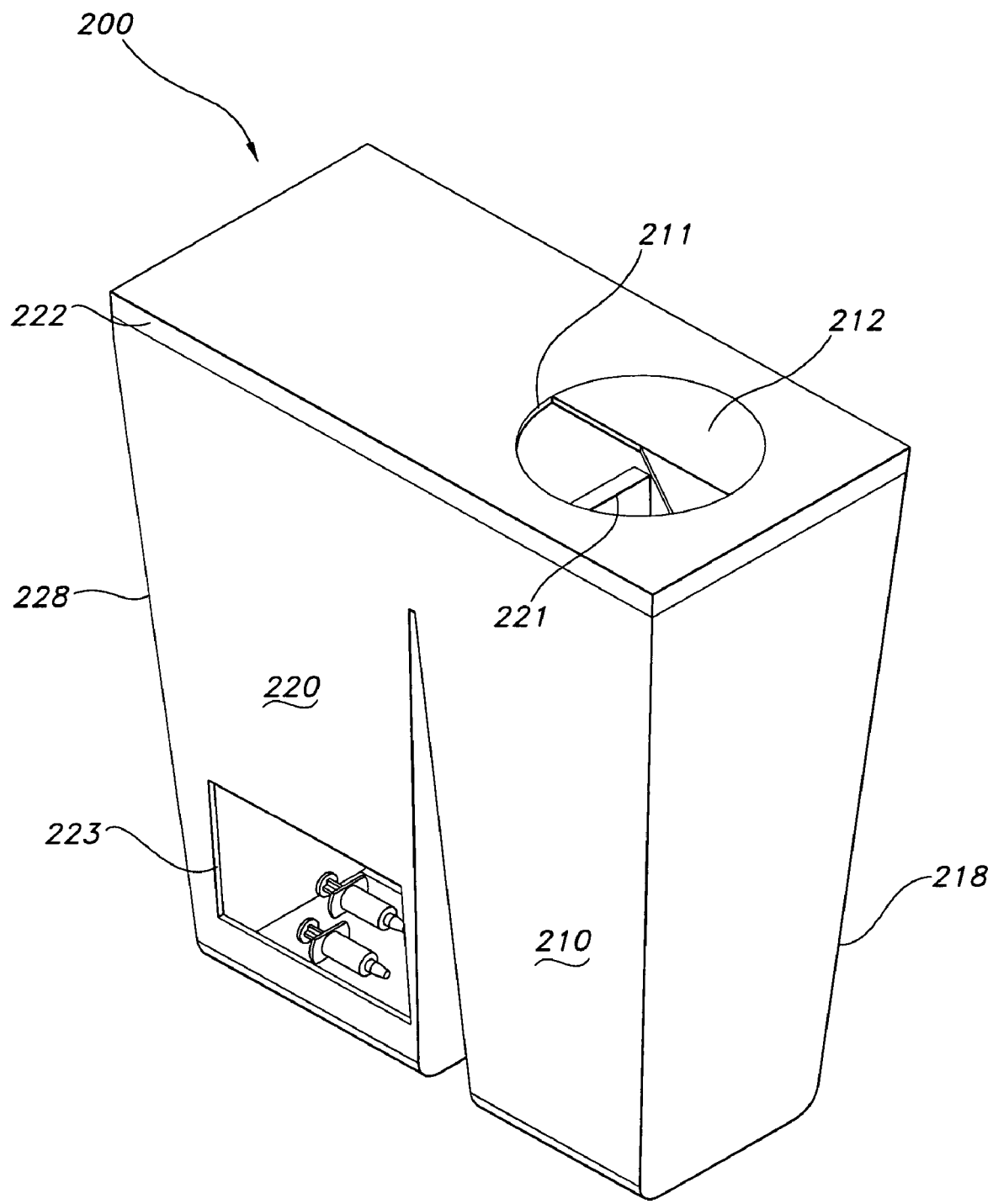
FIG. 4 is a perspective view of another embodiment of a medical implement dispensing and disposal system according to an aspect of this invention.
Figure 7:
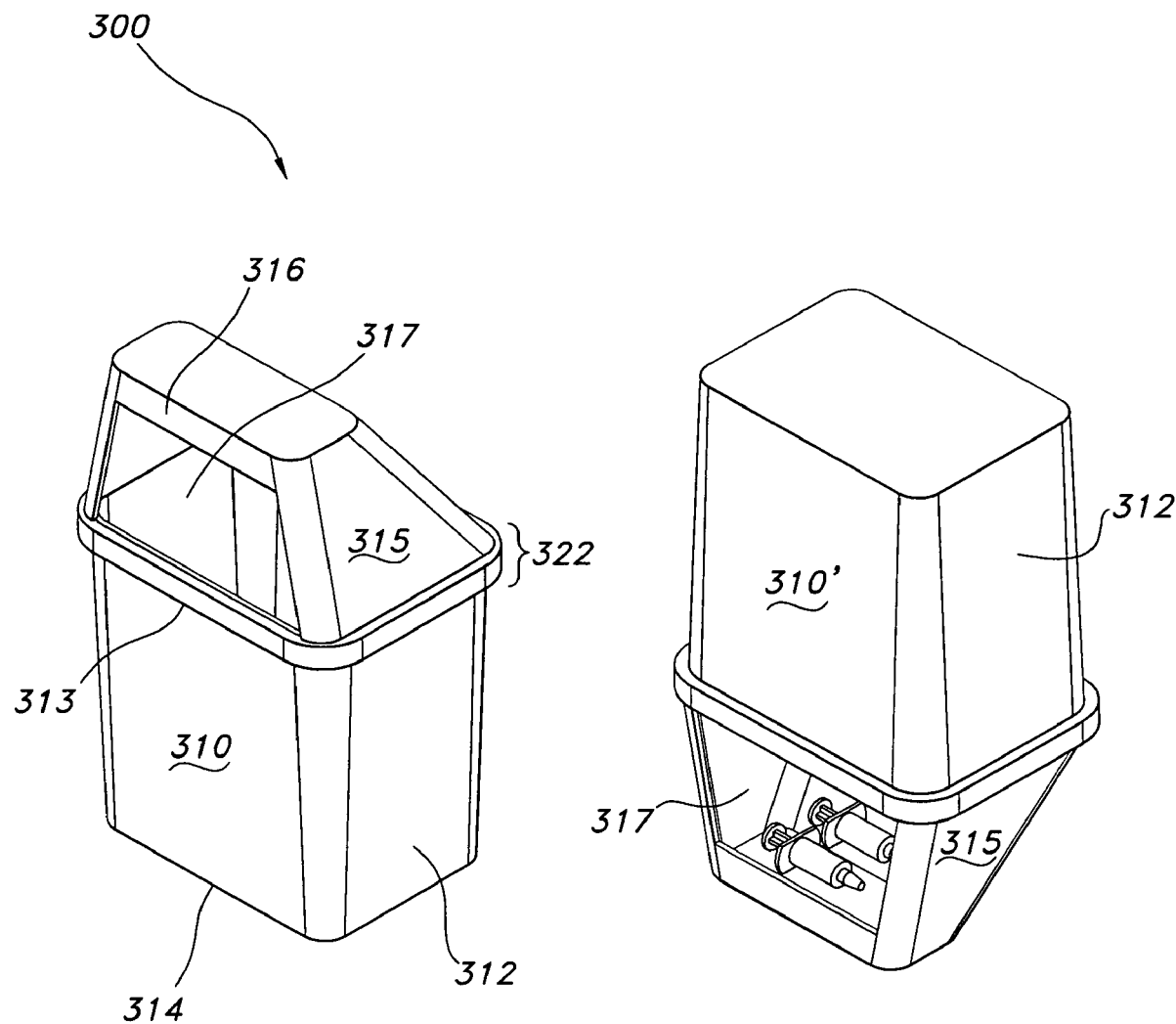
FIG. 7 is a perspective view of yet another embodiment of a medical implement dispensing and disposal system according to an aspect of this invention.

Although an enclosure 130, 230, 330 is selected for illustration, an enclosure 130, 230, 330 is an optional component of the medical implement dispensing and disposal system 100, 200, 300. A medical implement dispensing and disposal system 100, 200, 300 may include only a dispensing chamber such as the one defined by the dispensing container 120, 220, 310' and a collection chamber such as the one defined by the collection container 110, 210, 310, as illustrated in FIGS. 1, 4 and 7.

Figure 2:
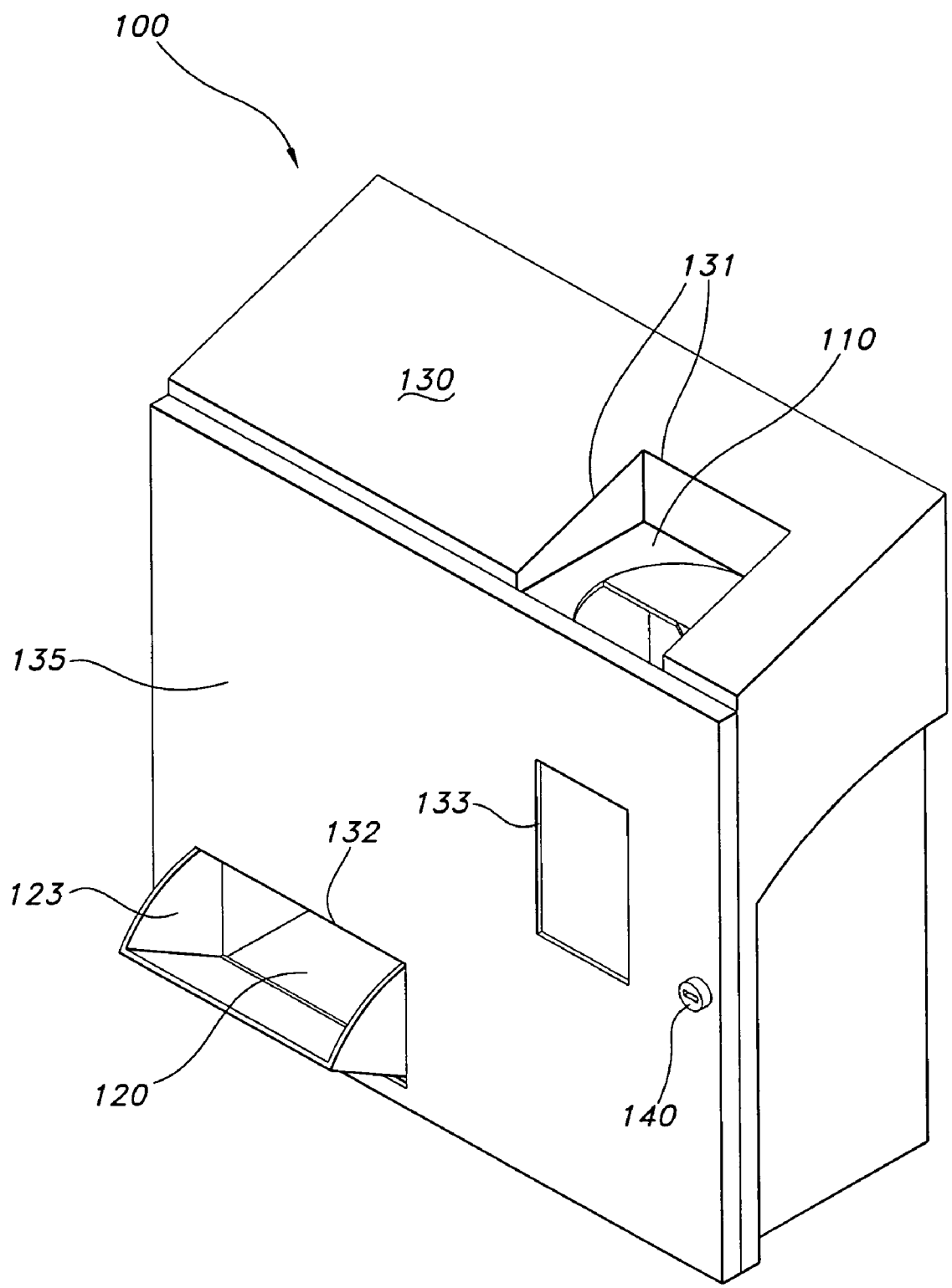
FIG. 2 is a perspective view of the embodiment illustrated in FIG. 1 mounted within a closed enclosure.
Figure 3:
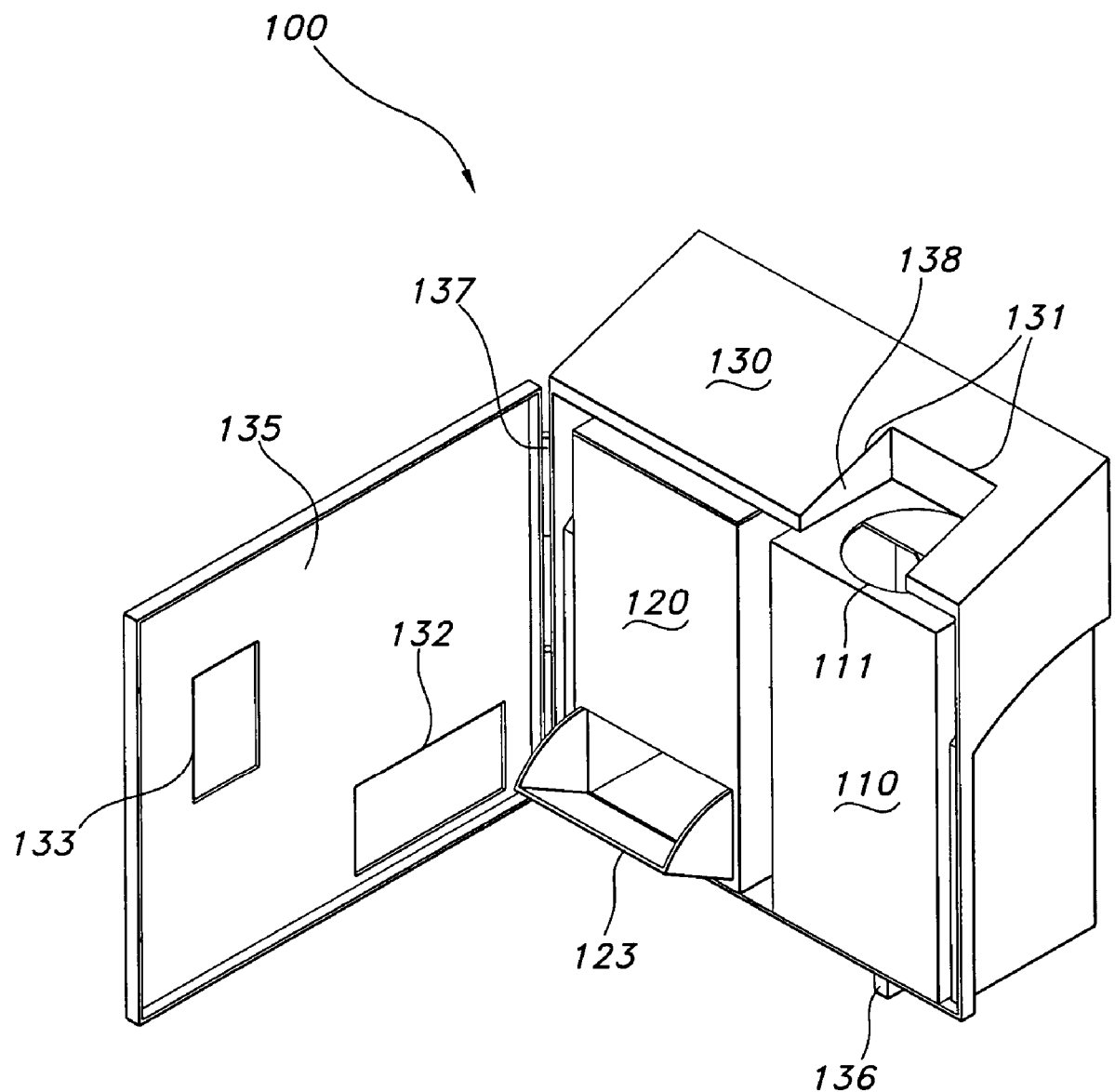
FIG. 3 is a perspective view of the embodiment illustrated in FIG. 1 mounted within an open enclosure.

Referring to the exemplary embodiment illustrated in FIGS. 1 through 3, more specifically FIG. 1, a medical implement dispensing and disposal system according to one aspect of this invention is generally designated by the numeral 100. The system 100 includes a collection chamber defined by a collection container 110 and a dispensing chamber defined by a dispensing container 120. The collection container 110 includes a body portion 118, a lid 112 and an inlet 111 formed in the lid 112. The dispensing container 120 includes a body portion 128, a lid 122, a chute 123 and an access opening 129.

The collection container 110 of the exemplary embodiment is configured to store soiled medical implements. The walls of the collection container 110 define an interior body portion 118 and compose the structure of the collection container 110. The soiled medical implements are stored within the interior body portion 118. A lid 112 is positioned on the top wall of the collection container 110 to provide access to the body portion 118. The lid 112 defines an inlet opening 111 for passage of the soiled medical implements into the body portion 118.

The lid 112 comprises all or a portion of the top wall of the collection container 110. In this embodiment, the lid 112 includes a slideable screen that is pivotable between an open position (as illustrated in FIG. 1) and a closed position. The position of the screen defines the size of the inlet opening 111 through which the soiled medical implements are passed. The user pivots the screen to close the inlet opening 111, for example, to restrict access to the interior body portion 118 filled with soiled medical implements. The user may also close the inlet opening 111 to prevent the leakage of soiled medical implement or contents thereof during transportation.

The lid 112 may be integrally formed with the top wall of the collection container. Alternatively, the lid 112 may be a discrete component mounted to the top wall of the collection container as shown in FIG. 1. The lid 112 can be mounted to the top wall of the collection container 110 using a hinge, adhesive, weld, clip, clamp or any other mechanical fastening method commonly known in the art. Although the lid 112 and integral inlet 111 are positioned on the top wall of the collection container 110 in this embodiment, the lid 112 and inlet 111 could be positioned on the upper portion of any side wall of the collection container 110 or at any other location, depending on other aspects of the design.

The dispensing container 120 of the exemplary embodiment is configured to dispense sterile, unused medical implements 124. The walls of the dispensing container 120 define the interior body portion 128 and compose the structure of the dispensing container 120. The sterile medical implements 124 are stored within the interior body portion 128. A lid 122 is hingedly connected to the top end of the dispensing container 120 by a hinge 121 to provide access to the interior body portion 128. The lid 122 pivots between an open position and a closed position (as illustrated in FIG. 1). In use, the lid 122 is pivoted to an open position to load sterile medical implements 124 into the interior body portion 128 of the dispensing container 120. The lid 122 is pivoted to a closed position, as shown, to inhibit access to the sterile medical implements 124.

An access opening 129 is formed on the lower end of a side wall to provide access to the sterile medical implements 124. An extendable chute 123 is hingedly connected to the bottom end of the dispensing container 120 by a hinge 125. The chute 123 comprises two side walls and a front wall extending between the side walls. The extendable chute 123 pivots between an open position (as illustrated in FIG. 1) and a closed position. In the open position, the extendable chute 123 facilitates the controlled passage of sterile medical implements 124 from the body portion 128 via access opening 129. In the open position, the chute 123 also forms an effective barrier to prevent the medical implements 124 from uncontrollably surging out of the access opening 129. In the closed position, the chute 123 obstructs the access opening 129, thereby preventing access to the sterile medical implements 124 within the body portion 128.

For the purposes of shipping and handling, the chute 123 and lid 122 are maintained in the closed position to prevent the escapement of pre-packaged sterile medical implements 124. The chute 123 and lid 122 are also maintained in the closed position to reduce the overall shipping size of the dispensing container 120. Although not illustrated, the chute 123 and lid 122 may incorporate locking features, to further prevent unauthorized access to the sterile medical implements 124.

In use and according to the exemplary embodiment illustrated in FIG. 1, one or more of the pre-packaged sterile medical implement(s) 124 are removed from the extended chute 123 of the dispensing container 120 for use, i.e. soiling. The formerly sterile medical implement(s), now soiled, are prepared for disposal and then inserted into the body portion 118 via inlet opening 111. After the body portion 118 of the collection container 110 is filled to capacity, the lid 112 is closed to prevent access to the body portion 118 through the inlet opening 111.

The containers 110, 120 of the exemplary embodiment may be formed by an injection molding process or blow molding process or any known forming process. Alternatively, the walls of the containers may be separate and adhered, welded, snapped and/or clipped together. The containers 110, 120 are desirably composed of a substantially leak resistant material such as polypropylene or polyethylene. The containers 110, 120 may be partially or completely transparent or translucent for the purpose of monitoring the level of medical implements within the containers.

Although not illustrated, a single universal container could incorporate the features of both containers 110 and 120. The universal container would provide both a lid 112 (with inlet opening 111) and an extendable chute 123. When used as a dispensing container, the extendable chute 123 of the universal container would be extended to an open position and the lid 112 would be rotated to a closed position. When used as a collection container, the extendable chute 123 of the universal container would be retracted to a closed position and the lid 112 would be rotated to an open position. Manufacturing, inventory and/or tooling a single universal dispensing/collection container in lieu of two separate containers could represent a significant cost savings.

Referring specifically now to FIGS. 2 and 3, the medical implement dispensing and disposal system 100 illustrated in FIG. 1 is mounted in an enclosure 130, according to one aspect of this invention. As mentioned previously, although an enclosure 130 is selected for illustration and included as a component of this exemplary embodiment, the enclosure 130 is an optional component of the dispensing and disposal system 100.

FIG. 2 illustrates the medical implement dispensing and disposal system 100 maintained in an enclosure 130, wherein the door 135 of the enclosure 130 is in a closed position. FIG. 3 illustrates the door 135 of the enclosure 130 in an open position. The enclosure 130 accommodates the containers 110, 120 for storage and safety purposes without inhibiting the functionality of the collection container 110 and the dispensing container 120. Accordingly, the enclosure 130 provides an opening 132 to accommodate the extendable chute 123 of the dispensing container 120. The opening 132 provides adequate clearance so that the extendable chute 123 may extend through the enclosure door 135 without obstruction (as illustrated in FIG. 2).

The enclosure 130 also provides an inlet opening 131 substantially aligned with the inlet opening 111 of the collection container 110 to permit the passage of soiled medical implements through the inlet opening 111. The inlet opening 131 includes a plurality of side walls 138 that extend into or toward the interior of the enclosure 130 to contact or terminate proximal the top side of the collection container 110. The side walls 138 prohibit the soiled medical implements from unintentionally descending into the interior of the enclosure 130 or entering the chute 123.

The enclosure 130 comprises five sidewalls and a hingedly connected door 135. Although the enclosure 130 comprises five sidewalls, the enclosure may have any number of sidewalls. The door 135 is hingedly connected to a sidewall of the enclosure 130, by a hinge 137, as illustrated in FIG. 3. The door 135 may be connected to any of the sidewalls of the enclosure 130, as the orientation and position of the door 135 is not limited to the illustration shown.

One or more supports 136 are provided on the base of the enclosure 130. The supports 136 are configured to maintain the enclosure 130 in an upright position when the enclosure 130 is mounted on a surface such as a floor or desk. Alternatively, although not shown, the rear wall of the enclosure 130 may provide holes, slots or brackets for mounting the enclosure 130 to a wall.

A window 133 is provided on the door 135 of the enclosure 130. The window facilitates the monitoring of soiled medical implements within the collection container 110 when the door 135 is in the closed position, as illustrated in FIG. 2. In use, a user monitors the level of the soiled medical implements within the collection container 110 to determine when to replace the collection container 110.

A lock 140 is provided on the door 135 of the enclosure 130 to prevent unauthorized access to the interior of the enclosure 130. The lock 140 engages with a side wall of the enclosure 130.

The enclosure 130 of the exemplary embodiment may be formed by an injection molding, blow molding, casting or other forming process. Alternatively, the walls of the enclosure may be separate and adhered, welded, snapped and/or clipped together. The enclosure 130 may be composed of a material such as polypropylene or polyethylene or other suitable material.

Figure 5:
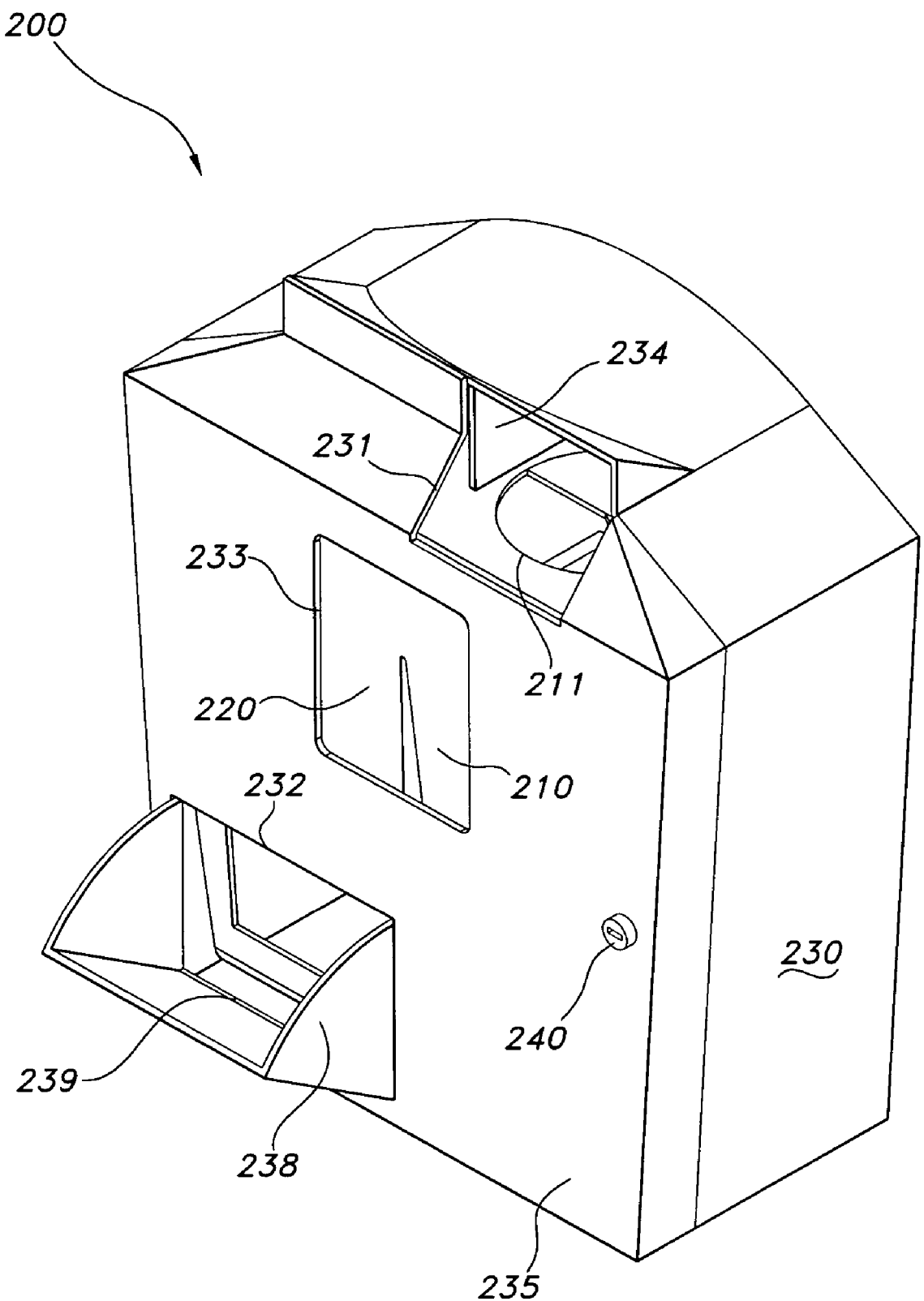
FIG. 5 is a perspective view of the embodiment illustrated in FIG. 4 mounted within a closed enclosure.
Figure 6:
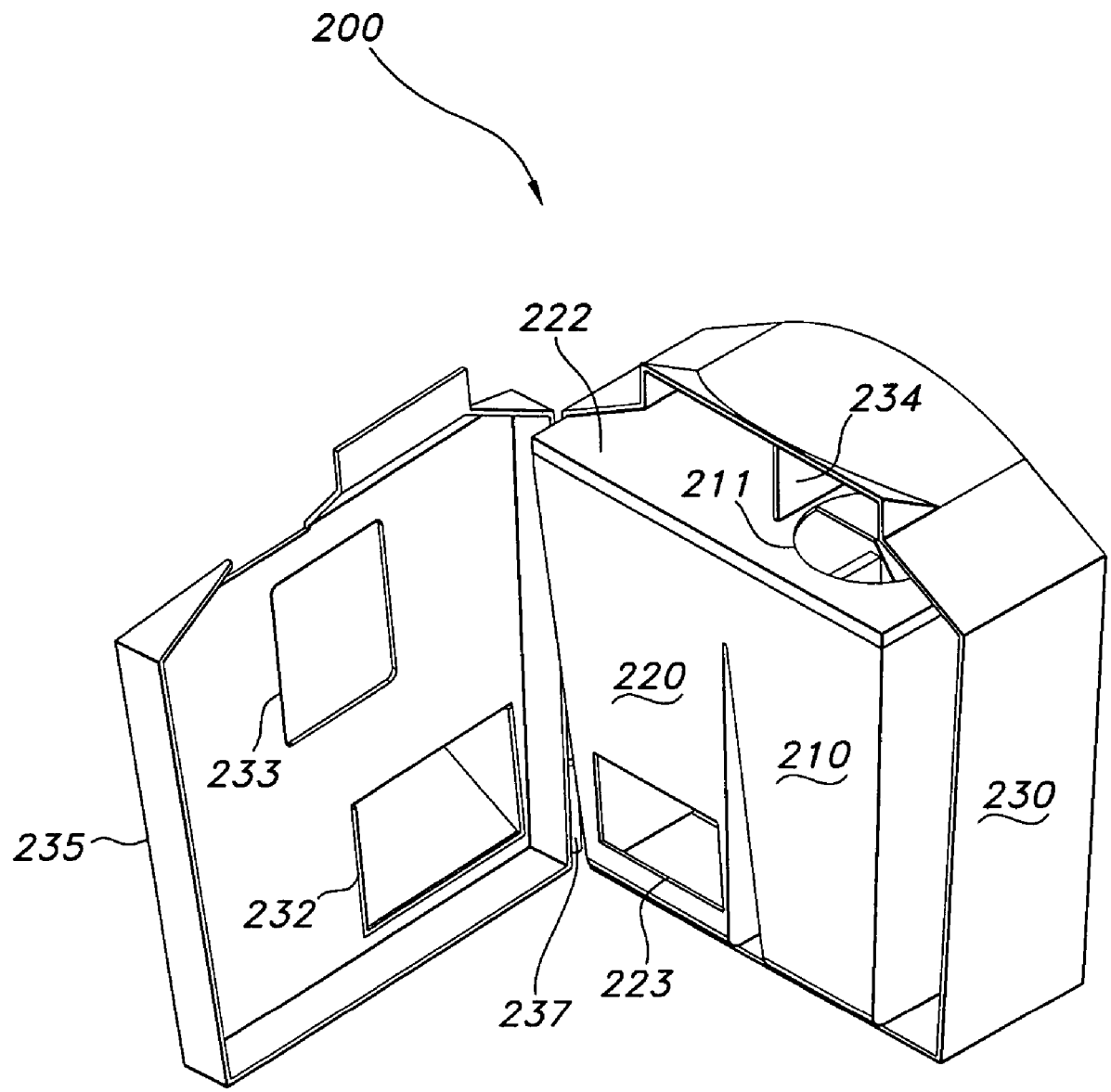
FIG. 6 is a perspective view of the embodiment illustrated in FIG. 4 mounted within an open enclosure.

Similar to the exemplary embodiment illustrated in FIGS. 1 through 3, another exemplary embodiment of a medical implement dispensing and disposal system is illustrated in FIGS. 4 through 6. The medical implement dispensing and disposal system 200 includes a collection container 210 defining a collection chamber configured to collect soiled medical implements and a dispensing container 220 defining a dispensing chamber configured to dispense medical implements. In this exemplary embodiment the dispensing container 220 and the collection container 210 are formed from a single unitized body. Manufacturing, inventory and/or tooling of a single dispensing/collection container in lieu of two separate containers could represent a significant cost savings. The dispensing container 220 includes a body portion 228 and an access opening 223. The collection container 210 includes a body portion 218. A lid 222 is mounted to the top end of the collection container 210 and the dispensing container 220.

Similar to the previous embodiment illustrated in FIGS. 1 through 3, the lid 222 incorporates a slideable screen 212 that is pivotable between an open position (as illustrated in FIG. 4) and a closed position. The position of the screen 212 defines the size of the inlet opening 211 through which the soiled medical implements are passed. The slideable screen 212 may be integral with the lid 222 or mounted (e.g. snapped or adhered) onto the lid 222 as illustrated in FIG. 4.

The collection container 210 and the dispensing container 220 are formed from a single unitized body. An interior wall 221, shown as a dotted line, is positioned within the interior of the containers and separates the collection container 210 from the dispensing container 220. The interior wall 221 prevents the integration of the soiled and sterile medical implements.

The access opening 223 accommodates the passage of sterile medical implements from the dispensing container 220. A lid 222 is provided to cover the exposed top side of the containers 210, 220. The lid 222 is mounted to the top side of the containers 210, 220 by any mechanical mounting means known in the art, e.g. tongue and groove, clips, clamps, welds, adhesive, etc.

The unitized containers 210, 220 of the exemplary embodiment may be formed by an injection molding process or blow molding process or other known manufacturing process. Alternatively, the walls of the containers may be separate and adhered, welded, snapped and/or clipped together. The containers 210, 220 are desirably composed of a substantially leak resistant material such as polypropylene or polyethylene. The containers 210, 220 may be partially or completely transparent or translucent for the purpose of monitoring the level of medical implements within the containers.

Referring specifically now to FIGS. 5 and 6, similar to the previous embodiment, the medical implement dispensing and disposal system 200 illustrated in FIGS. 5 and 6 is mounted in an enclosure 230. FIG. 5 illustrates the medical implement dispensing and disposal system 200 maintained in an enclosure 230, wherein the door 235 of the enclosure 230 is in a closed position. FIG. 6 illustrates the door 235 of the enclosure 230 in an open position. The door 235 is hingedly connected to the enclosure 230 by a hinge 237. A window 233 is provided on the door 235 for monitoring the soiled medical implements within the collection container 210. A lock 240 is also provided on the door 235 to prevent unauthorized access to the interior portion of the enclosure 230.

Unlike the previous embodiment however, the enclosure 230 of this exemplary embodiment incorporates the extendable chute 238. The chute 238 is hingedly connected to the door 235 by hinge 239 and aligned with the access opening 223 of the dispensing container 220. The extendable chute 238 facilitates the controlled passage of sterile medical implements 224 through an access opening 232 of the enclosure 230 and the access opening 223 of the dispensing container 220. In the open position, the chute 238 also forms an effective barrier to prevent the medical implements 224 from uncontrollably surging out of the access opening 223 of the dispensing container 220, while concurrently providing user access to the sterile medical implements 124. In the closed position, the chute 238 obstructs the access opening 223 of the dispensing container 220, thereby prohibiting unauthorized user access to the sterile medical implements 224. In the retracted position (i.e. closed position), the side walls of the chute 238 are positioned on either side of the dispensing container 220.

The enclosure 230 provides an opening 231 substantially aligned with the inlet opening 211 of the collection container 210 to permit the passage of soiled medical implements through the inlet opening 211. The inlet 231 of the enclosure 230 includes a plurality of side walls 234 extending into the interior of the enclosure 230. The side walls 234 are maintained in frictional contact with the lid 222 and provide a barrier to prohibit the soiled medical implements from unintentionally descending into the interior of the enclosure 230.

Figure 8:
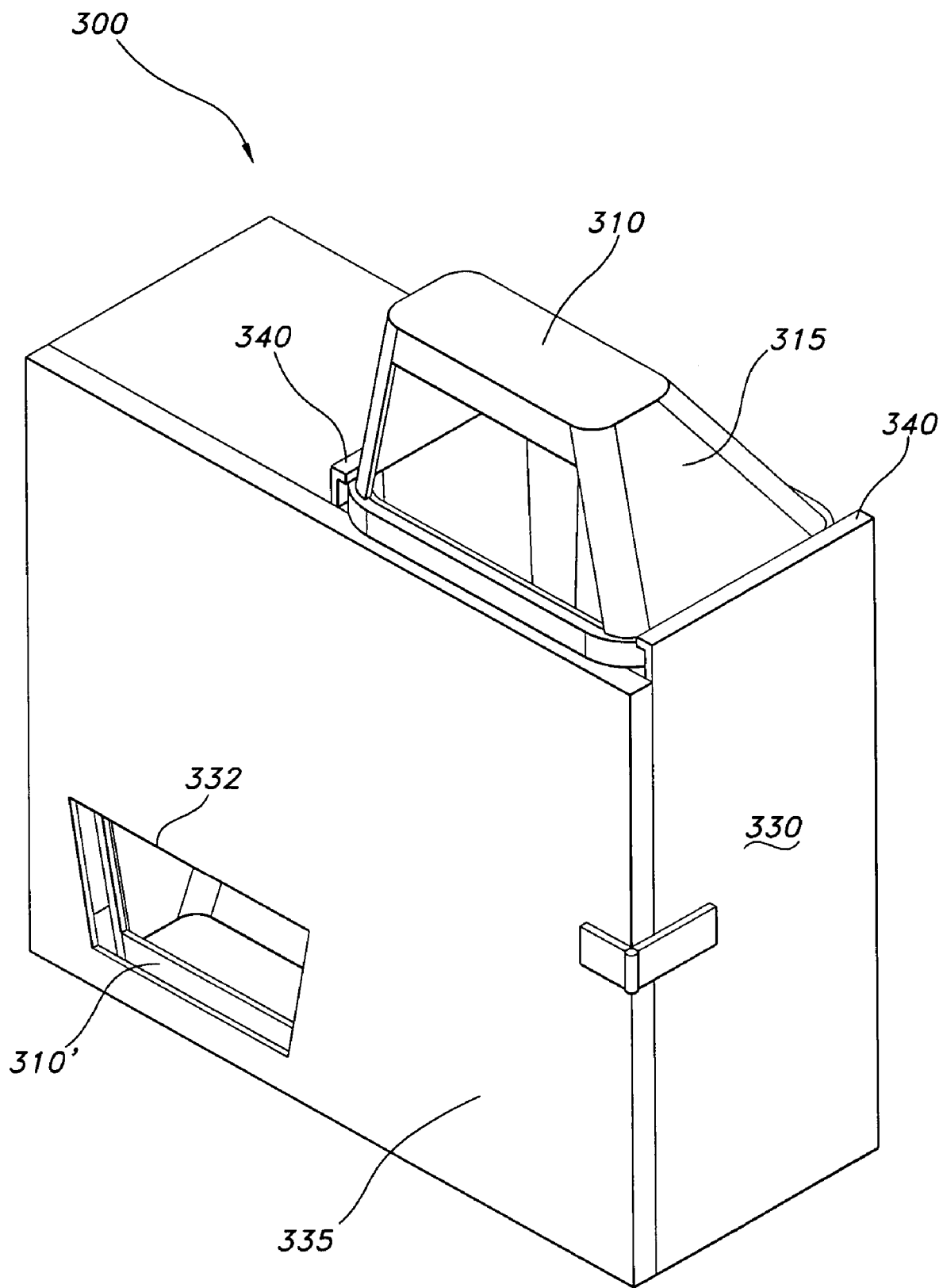
FIG. 8 is a perspective view of the embodiment illustrated in FIG. 7 mounted within a closed enclosure.
Figure 9:
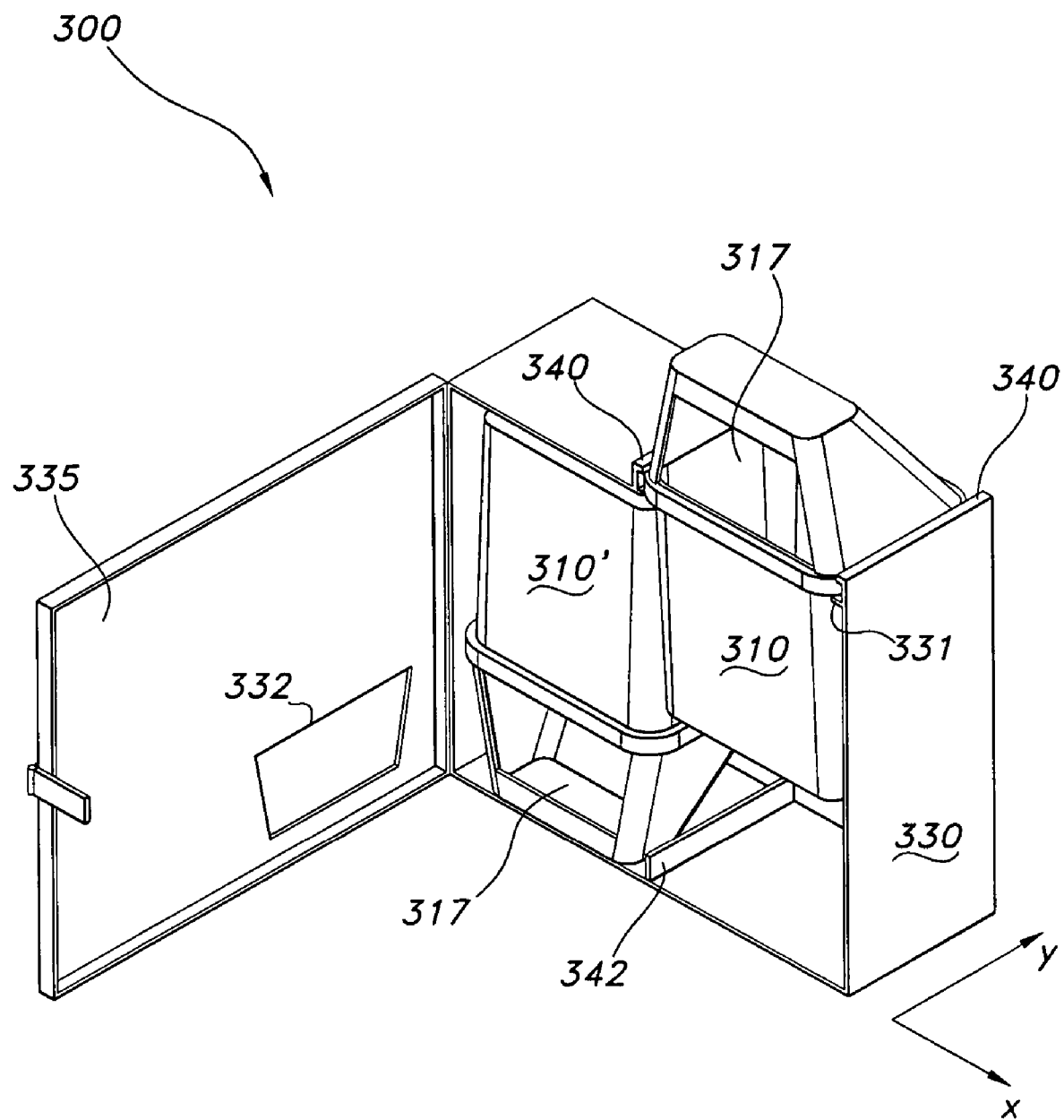
FIG. 9 is a perspective view of the embodiment illustrated in FIG. 7 mounted within an open enclosure.

Similar to the exemplary embodiments illustrated in FIGS. 4 through 6, another exemplary embodiment of a medical implement dispensing and disposal system is illustrated in FIGS. 7 through 9. The medical implement dispensing and disposal system 300 includes a collection container 310 defining a collection chamber configured to collect soiled medical implements and a dispensing container 310' defining a dispensing chamber configured to facilitate the distribution of medical implements. In this exemplary embodiment a single universal container is configured to be both a dispensing container 310' and a collection container 310. In one orientation the container operates as a dispensing container 310' and in another orientation the container operates as a collection container 310. Referring specifically to FIG. 7, the container shown to the left is oriented as a collection container 310 and the container shown to the right is oriented as a dispensing container 310'. The collection container 310 is oriented upright and the dispensing container 310' is oriented inverted.

The universal container 310, 310' may be advantageous from a manufacturing, inventory and/or tooling perspective. The fabrication of a single dispensing/collection container in lieu of two different containers may represent a significant cost savings.

The container 310, 310' includes a body portion 312 and a lid 315. The lid 315 is removably mounted to the top side 313 of the body portion 312. The lid 315 may be integrated with the body portion 312 or a separate component as illustrated in FIG. 7. The lid 315 includes an integral flange portion 322 positioned along the periphery of the lid 315. The purposed of the flange portion 322 will be described in further detail later. The lid 315 may be composed of sheet-metal or formed by a molding process.

A barrier wall 316 formed in the lid 315 extends into an opening 317. In the dispensing orientation (310'), the barrier wall 316 contains the sterile medical implements to facilitate the controlled passage of sterile medical implements through the opening 317 of the lid 315. The barrier wall 316 also forms an effective barrier to prevent the medical implements from uncontrollably surging out of the opening 317.

Figure 7A:
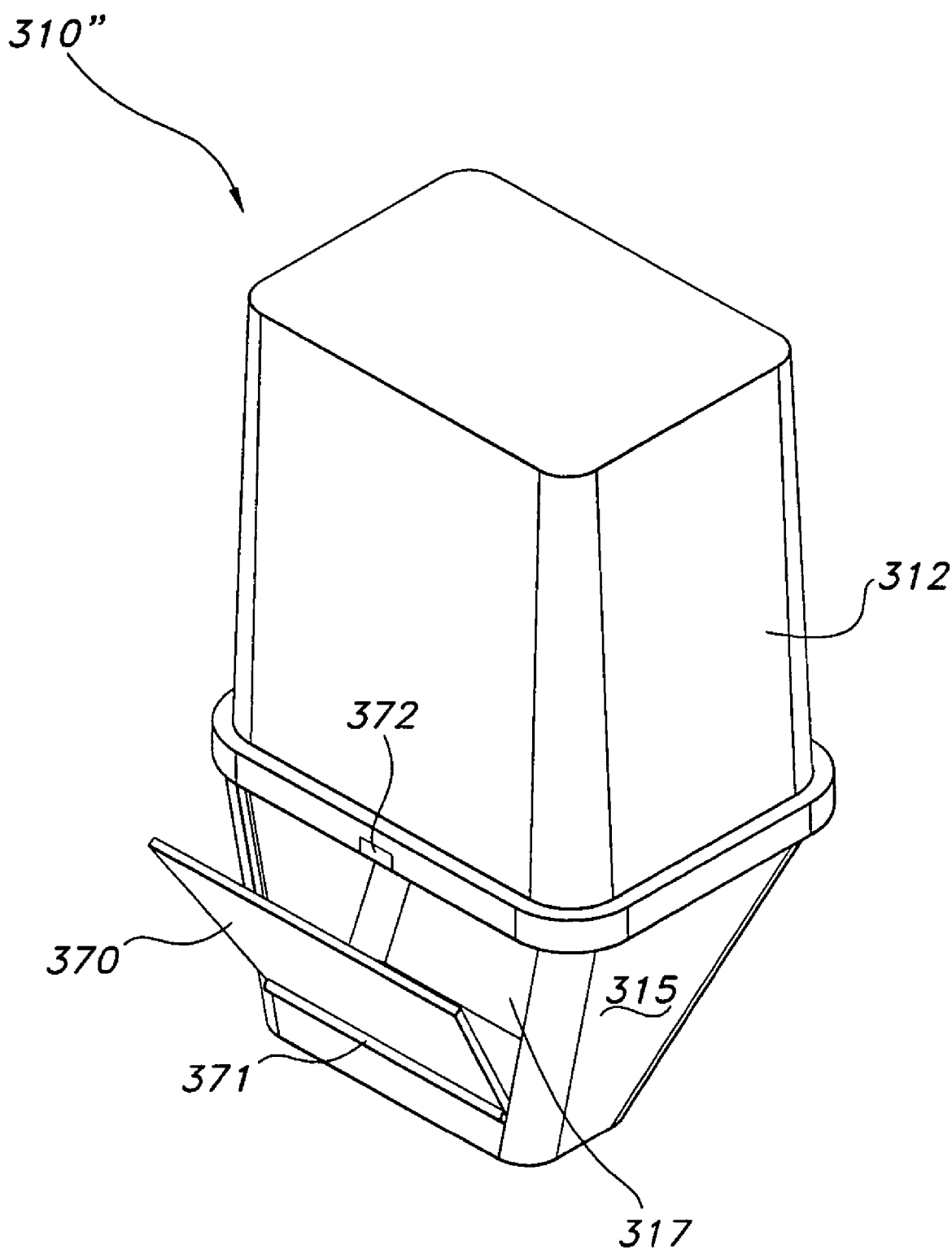
FIG. 7A is a perspective view of the embodiment illustrated in FIG. 7 in conjunction with a flip lid.

The exemplary embodiment of the dispensing container 310" illustrated in FIG. 7A includes a flip lid 370 pivotably coupled to the barrier wall 316. The flip lid 370 is configured to pivot between an open position and a closed position. The flip lid 370 illustrated in FIG. 7A is shown in a partially open position. Although the flip lid 370 selected for illustration is incorporated with a dispensing container 310", the flip lid 370 may also be incorporated with a collection container 310. In the open position the flip lid 320 either provides access to the sterile medical implements within the dispensing container 310" or the soiled medical implements within the collection container 310. In the closed position the flip lid 370 obstructs the opening 317 thereby prohibiting access to the soiled medical implements within the collection container 310 or the sterile medical implements within the dispensing container 310". A lock 372 is coupled to the barrier wall 316 to prevent unauthorized access to the containers 310, 310". The lock is especially advantageous to safely obstruct the opening 317 of the collection container 310 upon handling and transportation of the container 310.

Referring specifically now to FIGS. 8 and 9, similar to the previous embodiments the medical implement dispensing and disposal system 300 illustrated in FIGS. 8 and 9 are accommodated in an enclosure 330. FIG. 8 illustrates the medical implement dispensing and disposal system 300 maintained in an enclosure 330, wherein the door 335 of the enclosure 330 is in a closed position. FIG. 9 illustrates the door 335 of the enclosure 330 in an open position. As shown in FIG. 9, the dispensing container 310' is illustrated on the left hand side of the enclosure 330 in an inverted orientation and the collection container 310 is illustrated on the right hand side of the enclosure 330 in an upright orientation.

The enclosure 330 provides an opening 331 positioned to accommodate the lid 315 of the collection container 310. The enclosure 330 also provides an access opening 332 substantially aligned with the opening 317 of the dispensing container 310' to facilitate the passage of sterile medical implements from the dispensing container 310'. Two rail sections 340 accommodate the flange portions 322 of the collection container 310. The flange portions 322 engage with and translate along the rail sections 340. The two rail sections 340 limit the collection container 310 from shifting in the x direction. The door 335 and rear wall of the enclosure limit the collection container 310 from shifting in the y direction. A barrier 342 formed on the lower wall of the enclosure 330 limits the dispensing container 310' from shifting in the x direction. The door 335 and rear wall of the enclosure limits the dispensing container 310' from shifting in the y direction.

In use, after all of the sterile medical implements within the dispensing container 310' have been utilized and the collection container 310 is sufficiently filled with soiled medical implements, the filled collection container 310 is removed from the enclosure 330 and safely disposed of to provide space for an empty collection container 310. The empty dispensing container 310' is inverted to change its functionality from a dispensing container 310' to a collection container 310. The collection container 310, which was previously an empty dispensing container 310', is mounted on the right hand side of the enclosure 330 in an upright position. A new dispensing container 310' filled with sterile medical implements is mounted on the left hand side of the enclosure 330.

Referring to the embodiment illustrated in FIGS. 7 through 9, the sterile medical implements may be pre-packaged within the dispensing container 310' to facilitate quick installation of the system 300. The opening 317 may be sealed with a removable barrier to prevent the escapement of the sterile medical implements from the dispensing container 310' during shipment. It is contemplated that an enclosure 330 with or without a dispensing container 310' and/or a collection container 310 could be packaged and shipped to a user. It is also contemplated that an individual dispensing container 310' and/or a collection container 310 could be packaged and shipped to a user, with or without an enclosure 330.

Although this invention has been described with reference to particular embodiments selected for illustration in the Figures, it will be appreciated that many variations and modifications can be made to the systems 100, 200, 300 and the components thereof without departing from the spirit or the scope of this invention. For example, it should be noted that it is not required that the unused medical implements are sterile, as the dispensing container is configured to hold a medical implement in any condition. Although several molding processes are mentioned, the systems and components thereof are not limited to any specific manufacturing process or material. Additionally, although the collection and dispensing containers selected for illustration are shown side by side, the collection container may be positioned above the dispensing container, or vice versa.

What is claimed is:

1. A medical implement dispensing and disposal system comprising:
    an enclosure defining an interior and having a first opening for receiving soiled medical implements and a second opening for dispensing clean medical implements;
    a dispensing chamber removably positionable within the interior of the enclosure, the dispensing chamber being adapted to contain the clean medical implements and having an access opening for passage of the clean medical implements from the dispensing chamber, the access opening being positioned for alignment with the second opening of the enclosure to facilitate passage of the clean medical implements from the enclosure, the dispensing chamber having a top and a bottom;
    a disposal chamber removably positionable within the interior of the enclosure such that the disposal chamber is positionable adjacent the dispensing chamber, the disposal chamber being adapted to collect soiled medical implements, the disposal chamber having an inlet opening for passage of the soiled medical implements into the disposal chamber, the inlet opening being positioned for alignment with the first opening of the enclosure to facilitate passage of the soiled medical implements into the enclosure, the disposal chamber having a top and a bottom,
    the inlet opening of the disposal chamber being positioned at an elevation measured from the bottom of the disposal chamber that differs from an elevation of the access opening of the dispensing chamber measured from the bottom of the dispensing chamber, wherein the dispensing chamber and the disposal chamber are formed from a single unitized body; and
    a lid covering the dispensing chamber and the disposal chamber, the lid including a door positioned proximal of the inlet opening of the disposal chamber, the door having an open position configured to permit access to an interior of the disposal chamber and a closed position configured to inhibit access to the interior of the disposal chamber, the door being mounted for rotation between the open and closed positions.

2. The medical implement dispensing and disposal system of claim 1, further comprising an interior wall portion separating the dispensing chamber and the disposal chamber.

3. The medical implement dispensing and disposal system of claim 1, the inlet opening being positioned on an upper portion of the disposal chamber and the access opening being positioned on a lower portion of the dispensing chamber.

4. The medical implement dispensing and disposal system of claim 1, the inlet opening of the disposal chamber being positioned on or adjacent the top of the disposal chamber.

5. The medical implement dispensing and disposal system of claim 1, the access opening of the dispensing chamber being positioned on or adjacent the bottom of the disposal chamber.

6. The medical implement dispensing and disposal system of claim 1 wherein the bottom of the dispensing chamber is substantially aligned with the bottom of the disposal chamber.

7. A medical implement dispensing and disposal system comprising:
    an enclosure having an interior;
    a disposal chamber positioned in the interior of the enclosure, the disposal chamber defining an inlet opening for passage of soiled medical implements into the disposal chamber; and
    a dispensing chamber positioned in the interior of the enclosure adjacent the disposal chamber, the dispensing chamber defining an access opening for passage of clean medical implements from the dispensing chamber; and
    a lid mounted to the dispensing chamber and the disposal chamber, the lid including a door positioned proximal the inlet opening of the disposal chamber, the door having an open position configured to permit access to an interior of the disposal chamber and a closed position configured to inhibit access to the interior of the disposal chamber;
    the enclosure defining a first opening substantially aligned with the inlet opening of the disposal chamber and the door of the lid for passage of the soiled medical implements into the disposal chamber and the enclosure defining a second opening substantially aligned with the access opening of the dispensing chamber for passage of the clean medical implements from the dispensing chamber.

8. The medical implement dispensing and disposal system of claim 7, the disposal chamber and the dispensing chamber being formed from a single unitized body.

9. The medical implement dispensing and disposal system of claim 7, further comprising a door mounted to the enclosure to provide access for insertion of the dispensing and disposal chambers into the interior of the enclosure and for removal of the dispensing and disposal chambers from the interior of the enclosure.

10. The medical implement dispensing and disposal system of claim 7, further comprising a moveable door mounted to the enclosure, the moveable door having an open position to provide access for passage of the clean medical implements from the dispensing chamber and a closed position to inhibit passage of the clean medical implements from the dispensing chamber.

11. The medical implement dispensing and disposal system of claim 7, the first opening of the enclosure being defined in an upper portion of the enclosure and the second opening of the enclosure being defined in a lower portion of the enclosure.

12. The medical implement dispensing and disposal system of claim 7 further comprising a port in the enclosure configured to facilitate monitoring of the soiled medical implements.

13. The medical implement dispensing and disposal system of claim 7, wherein the first opening and the second opening of the enclosure are both forward facing.

14. A sharps dispensing and disposal system configured for mounting within an interior of an enclosure having a first opening for receiving soiled sharps and a second opening for dispensing sharps, the sharps dispensing and disposal system comprising:
a dispensing chamber configured to be substantially enclosed within the interior of the enclosure and removed from the interior of the enclosure, the dispensing chamber being adapted to contain clean sharps and having an access opening for passage of the clean sharps from the dispensing chamber, the access opening being positioned for alignment with the second opening of the enclosure to facilitate passage of the clean sharps from the enclosure;
at least one clean sharp contained within the dispensing chamber;
a disposal chamber configured to be substantially enclosed within the interior of the enclosure adjacent the dispensing chamber and removed from the interior of the enclosure, the disposal chamber being adapted to collect soiled sharps, the disposal chamber having an inlet opening for passage of the soiled sharps into the disposal chamber, the inlet opening being positioned for alignment with the first opening of the enclosure to facilitate passage of the soiled sharps into the enclosure, the inlet opening of the disposal chamber being positioned at a different elevation than the access opening of the dispensing chamber;
wherein the dispensing chamber and the disposal chamber are formed from a single unitized body; and
an enclosure defining an interior and having a first opening for receiving the soiled sharps and a second opening for dispensing the clean sharps.

15. The sharps dispensing and disposal system of claim 14, further comprising a lid covering the dispensing chamber and the disposal chamber.

16. The sharps dispensing and disposal system of claim 15, the lid including a door positioned proximal the inlet opening of the disposal chamber, the door having an open position configured to permit access to an interior of the disposal chamber and a closed position configured to inhibit access to the interior of the disposal chamber.

17. The sharps dispensing and disposal system of claim 14, wherein the inlet opening is positioned on an upper portion of the disposal chamber and the access opening is positioned on a lower portion of the dispensing chamber.

18. The sharps dispensing and disposal system of claim 14, wherein the dispensing chamber and the disposal chamber are configured and dimensioned for removable positioning within the interior of the enclosure.

* * * * *